United States Patent
Wagner

(10) Patent No.: US 6,382,976 B1
(45) Date of Patent: May 7, 2002

(54) DENTAL IMPLANT HAVING ROUND BOTTOM WITH FLUID DIRECTING CHANNELS

(75) Inventor: William R. Wagner, Escondido, CA (US)

(73) Assignee: Sulzer Dental Inc., Carlsbad, CA (US)

(*) Notice: Subject to any disclaimer, the term of this patent is extended or adjusted under 35 U.S.C. 154(b) by 0 days.

(21) Appl. No.: 09/776,804

(22) Filed: Feb. 5, 2001

(51) Int. Cl.⁷ ............................................... A61C 8/00
(52) U.S. Cl. ...................................................... 433/174
(58) Field of Search ............................................. 433/174

(56) References Cited

U.S. PATENT DOCUMENTS

| | | | |
|---|---|---|---|
| 4,713,004 A | 12/1987 | Linkow et al. | 433/174 |
| D296,362 S | 6/1988 | Branemark | D24/33 |
| 4,793,808 A | 12/1988 | Kirsch | 433/173 |
| 5,064,425 A | 11/1991 | Branemark e al. | 606/72 |
| 5,269,685 A | 12/1993 | Jorneus et al. | 433/174 |
| 5,316,476 A | 5/1994 | Krauser | 433/173 |
| 5,409,072 A | 4/1995 | Enlund et al. | 175/71 |
| 5,415,545 A | 5/1995 | Shaw | 433/173 |
| 5,449,291 A | 9/1995 | Lueschen et al. | 433/173 |
| 5,604,429 A | 2/1997 | Blacklock | 433/174 |
| 5,628,630 A | 5/1997 | Misch et al. | 433/174 |
| 5,842,865 A * | 12/1998 | Bassett et al. | 433/174 |
| 5,897,319 A | 4/1999 | Wagner et al. | 433/174 |
| 5,915,967 A * | 6/1999 | Clokie | 433/174 X |
| 5,947,735 A * | 9/1999 | Day | 433/174 |

* cited by examiner

Primary Examiner—Nicholas D. Lucchesi
(74) Attorney, Agent, or Firm—Philip S. Lyren

(57) ABSTRACT

A self-tapping dental implant having a round bottom with channels that extend upwardly to communicate with bone cutting flutes horizontally disposed along a tapping end of the implant.

9 Claims, 2 Drawing Sheets

US 6,382,976 B1

DENTAL IMPLANT HAVING ROUND BOTTOM WITH FLUID DIRECTING CHANNELS

FIELD OF THE INVENTION

The present invention relates generally to a self-tapping dental implant having a round bottom with channels that extend upwardly to communicate with bone cutting flutes disposed along a tapping end of the implant.

BACKGROUND OF THE INVENTION

Self-tapping dental implants typically have sharp cutting edges or surfaces that cut and scrape bone as the implant is being rotated and inserted into the jawbone of a patient. These cutting surfaces can be quite sharp and can, in some instances, damage surrounding or adjacent tissue. For instance, the nasal sinus is lined by a membrane called the nasal or schneiderian membrane. If a self-tapping dental implant is incorrectly placed too deeply, then the cutting surfaces can tear or perforate this membrane. Such damage can cause severe bleeding within the sinus cavity.

Some prior self-tapping implants have a completely round bottom. The round bottom mitigates the risk that the cutting surfaces will damage surrounding tissue. At the same time though, a completely round bottom has disadvantages. For example, fluid and debris tend to collect at the bottom of the osteotomy site. In some instances, it is desirable to remove or irrigate this fluid and debris as the implant is being implanted. An implant having a completely round bottom cannot easily accomplish this task.

The present invention solves the problems discussed above with prior self-tapping dental implants and provides further advantages.

SUMMARY OF THE INVENTION

The present invention is directed toward a self-tapping dental implant having a rounded or blunt-nose bottom with a plurality of cavities or channels that extend along the bottom. These cavities extend upwardly to communicate with bone cutting flutes disposed along a tapping end of the implant. The rounded end of the implant is devoid of sharp edges, corners, or the like and thus is able to press lightly against delicate anatomical features without tearing, puncturing, or penetrating such features.

As another feature of the present invention, the cavities along the rounded bottom join to and communicate with the cutting flutes. As such, the cavities are able to move or irrigate fluids and debris into the cutting flutes while the implant is being implanted into the jawbone.

BRIEF DESCRIPTION OF THE DRAWINGS

The invention will hereafter be described with reference to the accompanying drawings.

DESCRIPTION OF THE PREFERRED EMBODIMENTS

Figure 1:
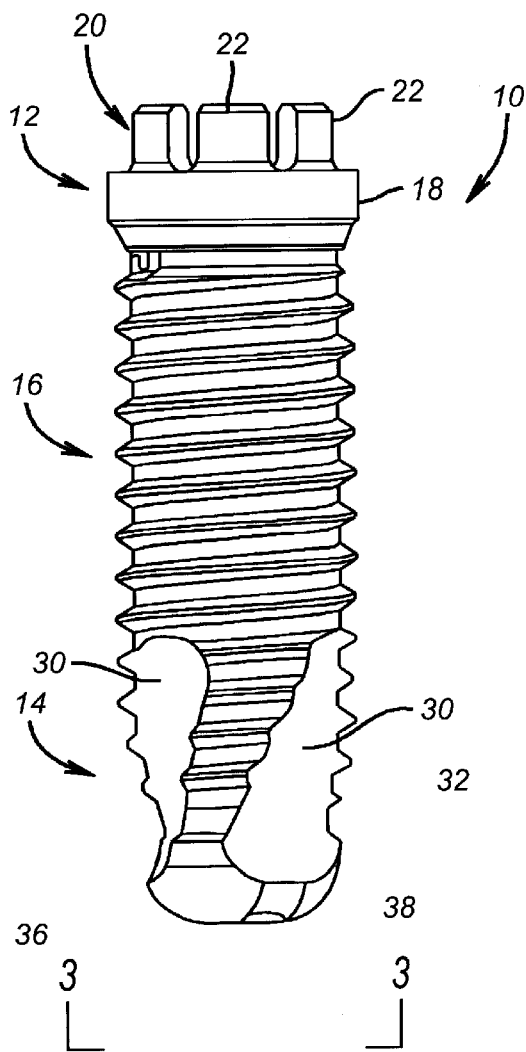
FIG. 1 is a side view of the dental implant according to the invention.

FIG. 1 shows a self-tapping implant at 10. Implant 10 has a generally elongated cylindrical configuration and includes a coronal end 12, a tapping end 14 oppositely disposed from the coronal end, and an externally threaded middle section 16 disposed between the two ends. The implant may have a coronal end and body similar to any one of various dental implants known to those skilled in the art and designed to be implanted into bone. For illustration purposes, implant 10 has a coronal end and body similar to a SPLINE TWIST dental implant manufactured by Sulzer Dental Inc. of Carlsbad, California. Further, the implant preferably is formed from titanium or one of its biocompatible alloys and may have any one of various surface coatings or surface textures, such as an as-machined surface or microtextured surface. Texturing of the threaded surface can be accomplished by a variety of processes known to those skilled in the art, such as grit-blasting with an abrasive medium or etching with a strong acid. Applicable surface coatings include calcium phosphates, such as hydroxylapatite and metallic coatings such as titanium or its oxides.

As shown, coronal end 12 includes an interface ring 18 and a prosthetic interface 20 that extends upwardly from interface ring. The prosthetic interface includes a plurality of splines or tines 22 for engaging a dental prosthesis or part of a prosthetic attachment system (not shown). These splines are taught in U.S. Pat. No. 5,449,291 entitled Dental Implant Assembly Having Tactile Feedback, issued to Lueschen et al.; this patent is fully incorporated herein by reference. The interface may be other configurations as well, such as internal or external polygons or other designs known to those skilled in the art.

Threaded middle section 16 is disposed between end 12 and end 14. This section includes external threads that helically extend around a cylindrical body portion of the implant. These threads may have any one of various configurations known to those skilled in the art.

Figure 2:
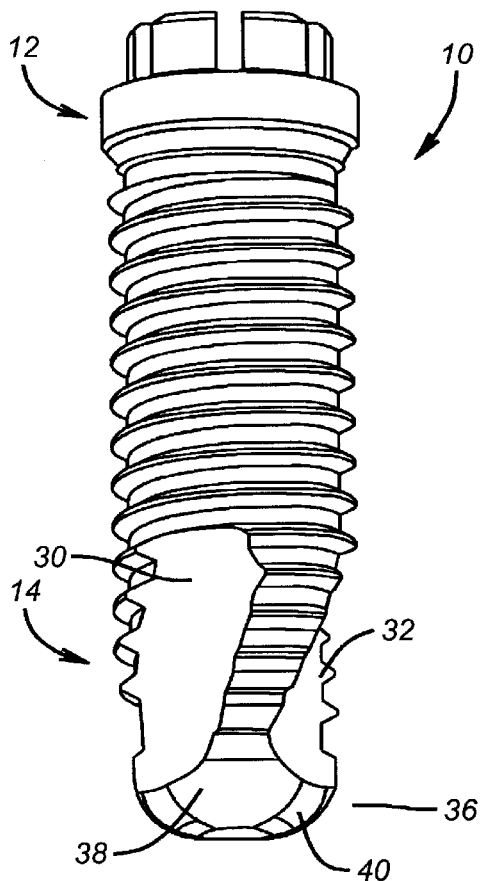
FIG. 2 is a slightly rotated view of the dental implant of FIG. 1.
Figure 3:
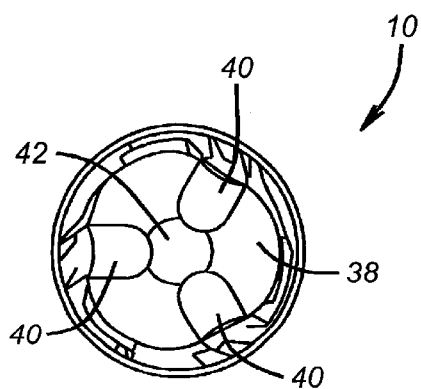
FIG. 3 is a bottom view of FIG. 1 taken along the line 3—3.

Reference is now simultaneously made to FIGS. 1–3. Tapping end 14 performs the tapping function of implant 10. In the preferred embodiment, this end includes three separate flute sections 30. The flutes extend upwardly and are symmetrically disposed around the body portion of the implant. Each flute forms a cavity generally having a curved configuration with a somewhat concave shape. A primary cutting edge or surface 32 extends along one side of the cavity. A smooth transition from the cutting edge to the cavity and additionally within the cavity itself helps to direct a smooth flow of bone chips away from the cutting edge and along the cavity. The flutes are more fully taught in U.S. Pat. No. 5,897,319 entitled Self-Tapping Implant with Helical Flutes, issued to Wagner et al.; this patent is fully incorporated herein by reference.

The distal portion of the tapping end has a rounded, hemispherical bottom 36. This bottom has a portion 38 with a smooth outer surface. Additionally, the bottom has three cavities or channels 40. Each cavity has a first end that converges at a distal tip 42 of the round bottom and a second end that connects to and communicates with a flute section 30. As shown in FIGS. 2 and 3, the distal tip is a flat, round surface or a concave surface. Further, although the figures depict three cavities and three flute sections, the present invention may incorporate one, two, three, four, or more cavities and flutes sections.

One important advantage of the cavities 40 is that they move or irrigate fluids (such as blood or cooling irrigation fluid used during the drilling process) and debris (such as bone chips and tissue) that collect in the prepared osteotomy. The cavities have a smooth, rounded, concave inner surface to facilitate movement of fluids and debris. The movement of these fluids and debris provides relief of hydrostatic pressure and facilitates insertion of the implant into the jawbone.

Another advantage of the present invention is that the cavities do not inhibit the self-tapping properties of the cutting flutes and implant. In fact, the communication between the cavities and cutting flutes enhance the ability of the implant to move bone chips, blood, and other fluids and debris toward the coronal end during surgical insertion. Fluid and debris, for example, are able to pass through the cavities and enter directly into the corresponding flute sections while the implant is being rotated and inserted into the jawbone.

Figure 4:
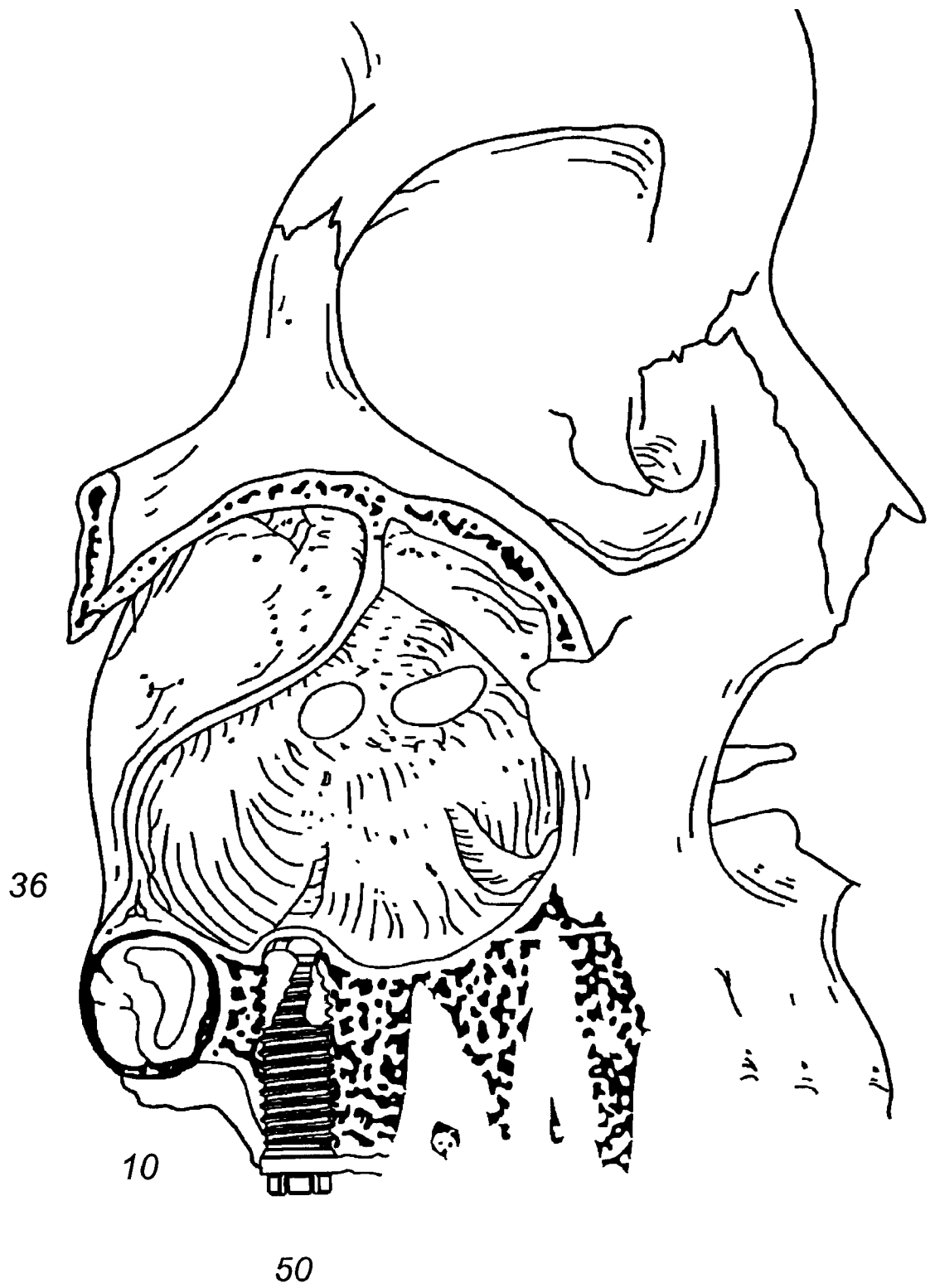
FIG. 4 is a partial cross-sectional view of a jawbone of human having the dental implant of the present invention implanted therein.

FIG. 4 shows a partial cross sectional view of a human jawbone 50 with the floor of the sinus and openings in maxillary sinus being labeled. In this figure, the implant 10 of the present invention is implanted into the jawbone with the round bottom 36 pressing against, but not penetrating or otherwise damaging, the floor of the sinus.

As shown in this figure, the rounded or blunt-nose bottom of the present implant has an important advantage. Specifically, the bottom of the implant is able to press lightly against the floor of the sinus without tearing, puncturing, or otherwise penetrating the sinus. In general, the tapping end of the implant is less likely to damage delicate anatomical features, such as the nasal or sinus membrane, mandibular nerve, or the like. At the same time though, the cavities in the round bottom are able to move fluids and debris away form the end of the implant during implantation.

Since certain changes may be made in the above-described apparatus without departing from the scope of the invention herein involved, all matter contained in the description or shown in the accompanying drawings should be interpreted as illustrative and not in a limiting sense.

What is claimed is:

1. A self-tapping dental implant for anchoring in a jawbone, comprising:

a generally cylindrical shaped body having a coronal end, a threaded middle portion, and a tapping end with three separate bone cutting flutes and a rounded bottom with three separate channels, wherein each channel joins to one of the flutes and has a first end that converges at a distal tip of the tapping end and a second end that joins to one of the flutes.

2. The self-tapping implant of claim 1 in which each channel has a smooth, rounded inner surface.

3. The self-tapping implant of claim 2 in which each channel is adapted to move fluids and bone debris from its first end at the distal tip, to its second end, and then into one of the flutes.

4. The self-tapping implant of claim 3 in which each channel extends upwardly from the distal tip and each flutes extends upwardly from the second end of the channel toward the coronal end of the implant.

5. The self-tapping implant of claim 4 in which each flute has a smooth rounded inner surface.

6. A dental implant for anchoring in a jawbone of a human, the dental implant comprising:

an elongated body having external threads, two separate helical flutes extending along the body and adapted to cut bone, and a blunt-nose hemispherical bottom with two separate cavities extending along the bottom and having an elongated channel shape with a smooth inner surface, wherein one end of each cavity joins to one end of each flute.

7. The dental implant of claim 7 in which the cavities are adapted to irrigate fluids into the flutes.

8. The dental implant of claim 7 in which the bottom has a portion with a smooth outer surface and a distal tip with a flat or a concave surface.

9. The dental implant of claim 8 in which one end of each cavity extends from the flat surface.

* * * * *